US 7,698,596 B2

(12) United States Patent
Busch et al.

(10) Patent No.: US 7,698,596 B2
(45) Date of Patent: Apr. 13, 2010

(54) MEDICAL DEVICE FOR DIAGNOSTICS OR THERAPY

(75) Inventors: Erik Busch, Malvern, PA (US); Peter Soukal, Schwarzenbruck (DE)

(73) Assignee: Siekens Aktiengesellschaft, Munich (DE)

( * ) Notice: Subject to any disclaimer, the term of this patent is extended or adjusted under 35 U.S.C. 154(b) by 1007 days.

(21) Appl. No.: 10/981,294

(22) Filed: Nov. 4, 2004

(65) Prior Publication Data

US 2005/0177342 A1 Aug. 11, 2005

(30) Foreign Application Priority Data

Nov. 6, 2003 (DE) ................. 103 51 782

(51) Int. Cl.
*G06F 11/00* (2006.01)
(52) U.S. Cl. ............... 714/26; 714/57; 702/183
(58) Field of Classification Search .......... 714/26, 714/57; 700/26, 110; 702/183
See application file for complete search history.

(56) References Cited

U.S. PATENT DOCUMENTS

| 4,881,230 | A | 11/1989 | Clark et al. |
| 5,600,574 | A | 2/1997 | Reitan |
| 6,035,328 | A | 3/2000 | Soukal |
| 6,414,466 | B1 * | 7/2002 | Ida ............................ 320/132 |
| 6,509,914 | B1 * | 1/2003 | Babula et al. .............. 715/762 |
| 6,810,391 | B1 | 10/2004 | Birkhoelzer et al. |
| 6,856,825 | B2 * | 2/2005 | Hahn ......................... 600/425 |
| 6,893,395 | B1 | 5/2005 | Kraus et al. |
| 2002/0049562 | A1 * | 4/2002 | Hahn ......................... 702/183 |
| 2007/0153329 | A1 * | 7/2007 | Sugawara et al. ......... 358/1.15 |

FOREIGN PATENT DOCUMENTS

| DE | 198 42 046 A1 | 3/2000 |
| DE | 199 30 263 A1 | 12/2000 |
| EP | 0 630 146 B1 | 12/1994 |
| WO | WO 03/043494 A1 | 5/2003 |

OTHER PUBLICATIONS

"AXIOM Artis *d*FC and AXIOM Artis *d*BC", Siemens AG, Medical Solutions, Order No. A91100-M1400-B151-1-7600, 24 pages, CC 64151 WS 95935, Erlangen, Germany.

* cited by examiner

*Primary Examiner*—Yolanda L Wilson

(57) ABSTRACT

The invention relates to a medical device for diagnostics and/or therapy with a system, with a device for self-analysis of the systems and creation of system internal status messages, with a device for interpretation of the system-internal status messages, with associated storage means for special technical and application knowledge, with an operating console for output of interpreted status messages and input of instructions, where the device for interpretation is embodied such that the system-internal status messages are converted on the basis of specialist technical and application knowledge into the interpreted status messages.

17 Claims, 3 Drawing Sheets

MEDICAL DEVICE FOR DIAGNOSTICS OR THERAPY

CROSS REFERENCE TO RELATED APPLICATIONS

This application claims priority to the German application No. 10351782.0, filed Nov. 6, 2003 and which is incorporated by reference herein in its entirety.

FIELD OF INVENTION

The invention relates to a medical device for diagnostics and/or therapy, with a system with facilities for self-analysis of the system and for generating internal status messages, and with an operating console for output of status messages and input of instructions as well as all special systems for medical imaging.

BACKGROUND OF INVENTION

Coronary heart disease (CHD) is one of the most frequent fatal illnesses and is on a rising trend. Examination of the coronary arteries with contrast means using x-ray imaging, known as coronary angiography, can be used for the diagnosis of coronary heart disease using a heart catheter. This method simultaneously makes it possible to treat coronary arteries with what is known as a balloon catheter (PTCA) with/and without Stentt inserts (mostly a wire mesh expansion). This diagnosis and therapy is undertaken at a cardiac catheterization unit (LHK). This type of cardiac catheterization unit is known from the brochure "AXIOM Artis dFC and AXIOM Artis dBC" from Siemens Medical Solutions, Order No.: A91100-M1400-B151-1-7600, print reference CC 64151 WS 05035 and is shown as an example in FIG. 1. The LHK features a biplane, schematically-represented x-ray diagnosis device 1 with two C-arms 2 and 3 at the ends of each of which x-ray emitters 4 and 5 as well as opposite them in a known way x-ray detectors 6, for example flat detectors, are accommodated. Furthermore the x-ray diagnostic device 1 is provided with a patient support table 8. To observe the examination a monitor holder or monitor traffic light 9 with in this example four monitors 10 is provided. A normal LHK however features six displays in the examination room.

In an adjacent control room there is an operating console 11 for communication with the system for the purposes of controlling C-arms 2 and 3, for generating the images and for processing them. Usually an operating console 11 is provided with two displays in the control room of an LHK.

SUMMARY OF INVENTION

Usually the system status is checked during the operation of the medical device. Deviations from the normal system status are generally communicated using short messages couched in technical terms. Self-analysis functions of the system register deviations from the normal system status and give such messages system-internal names with various cryptic error codes.

It cannot be assumed that medical users automatically have the ad-hoc knowledge of the technical engineering and application information concerning all aspects of all functions of the systems and the associated messages.

For this reason this technical engineering and application knowledge has to date been imparted to medical users by means of training courses and multimedia data media. The large amount of time expended on training and the consequent loss of earnings for providers of medical services resulting from the absence of medical personnel, the turnover rate among staff and the lack of remuneration for additional courses prevent ongoing training, so that this situation results in a reduction of the level of training.

An object of the invention is to develop a medical device of the type described in the introductory section of this document in such a way that even medical staff with little training can operate the medical device without problems.

The object is achieved by the claims, especially by providing a device for interpretation of the system-internal status messages as well as associated storage means for special technical and application knowledge, with said interpretation device being embodied such that the system-internal status messages are interpreted on the basis of the special technical and application knowledge into interpreted status messages. Using existing device processors the messages can be linked to the corresponding, electronically-stored expert knowledge.

It has proved advantageous for the device for self-analysis of the system and generation of system-internal status messages to be embodied such that it detects deviations from the normal system status and identifies these within the system using various cryptic error codes.

In an advantageous way the device for interpretation of the system-internal status messages can link the error code with the special technical engineering and application knowledge stored in the storage means and provide an output of generally understandable information about the system status and/or proposals for rectifying deviations.

In accordance with the invention the output can be visual, for example using displays on the monitor, projections and/or information printed out on a printer.

Alternatively or simultaneously the information can be output in sensory form using Braille.

A further option is audio output using tone modulation (speech) by means of loudspeakers built into the operating console.

It has proved advantageous for the output to be provided as a message to the service provider, for example by e-mail with the error log appended to it and/or as sound and/or text messages via radio networks.

BRIEF DESCRIPTION OF THE DRAWINGS

The invention is explained below in greater detail on the basis of the exemplary embodiments shown in the drawing. The diagrams show.

DETAILED DESCRIPTION OF INVENTION

Figure 1:
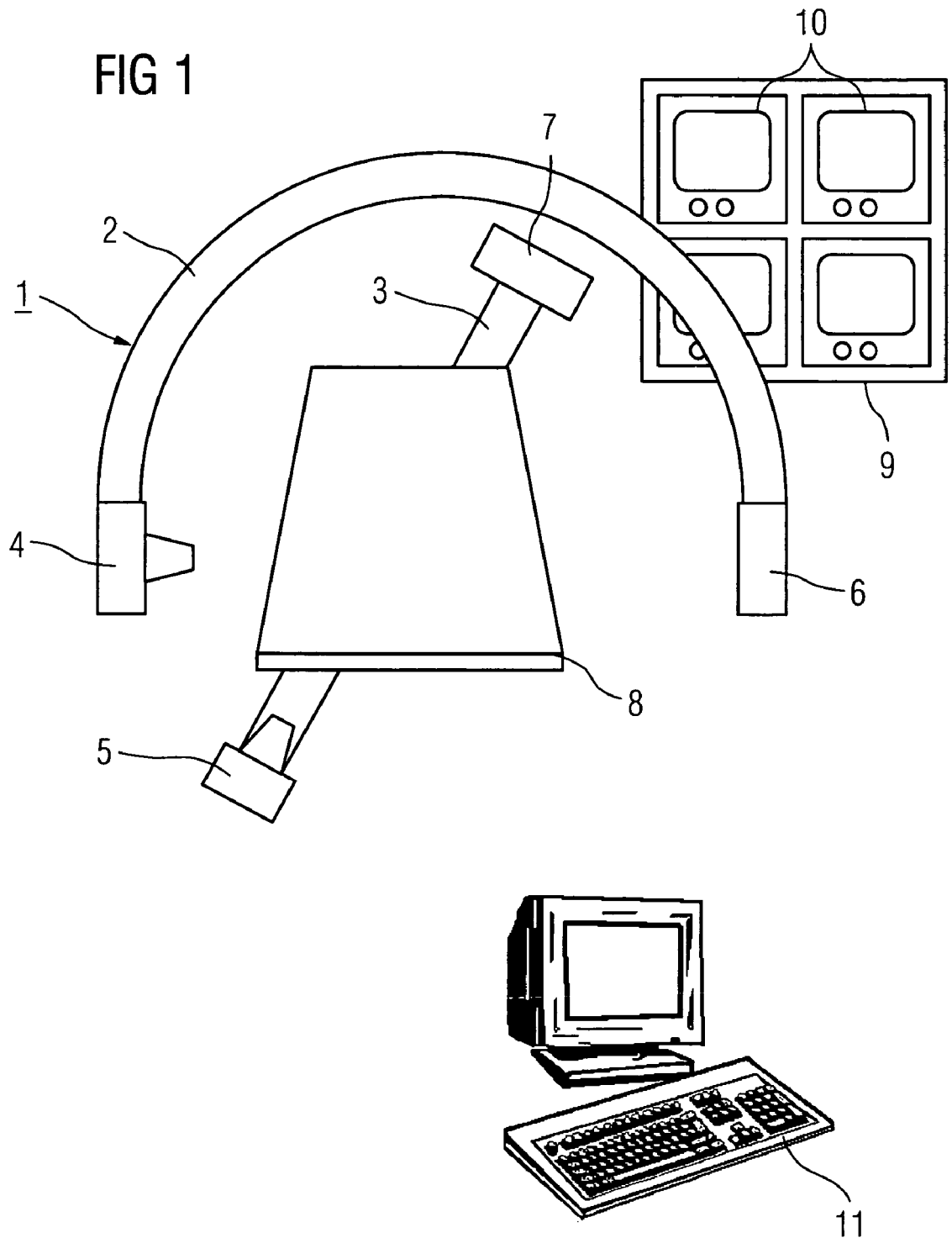
FIG. 1 a known cardiac catheterization unit (LHK)
Figure 2:
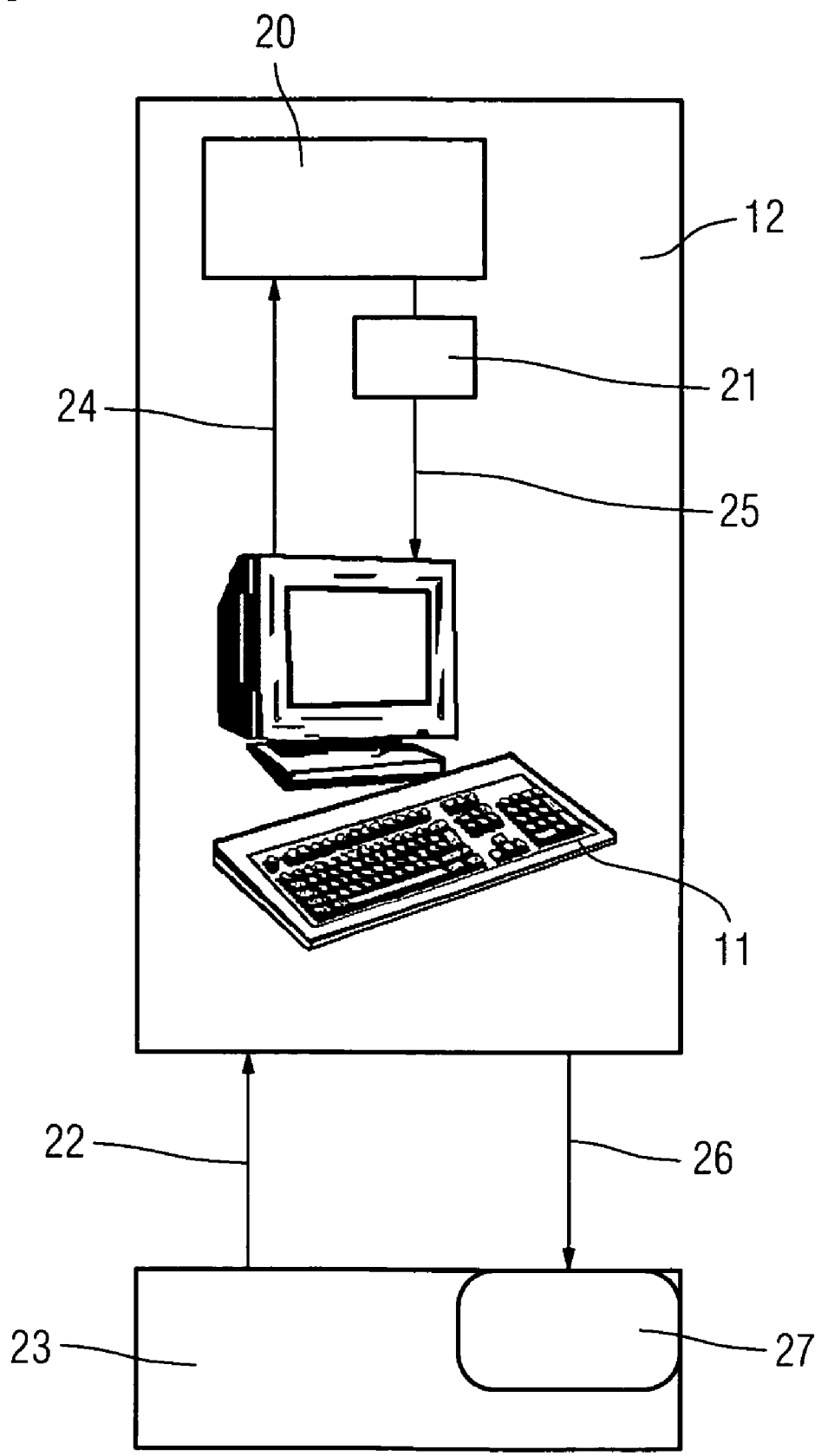
FIG. 2 a known workflow of a medical system, for example of the LHK shown in FIG. 1, and FIG. 3 a workflow in accordance with the invention of the LHK shown in FIG. 1.

FIG. 2 shows the previously known situation (workflow) which is important for operation of a medical diagnostic device. From the operating console 11 of medical systems 12 and special systems what are known as modalities for imaging and therapy, for example CT, MR, US, Nuc or x-ray, are controlled. This is done by specially trained medical personnel 23 entering instructions 23 via control commands 24. System-internal status messages 25 of a device 21 for self-analysis of the medical systems are reproduced acoustically or visually as status messages 26 by the operating console 11 and recorded by the medical operating personnel 23. They use the special knowledge 27 acquired in their training to interpret the status messages 26 and convert them into instructions 22.

Figure 3:
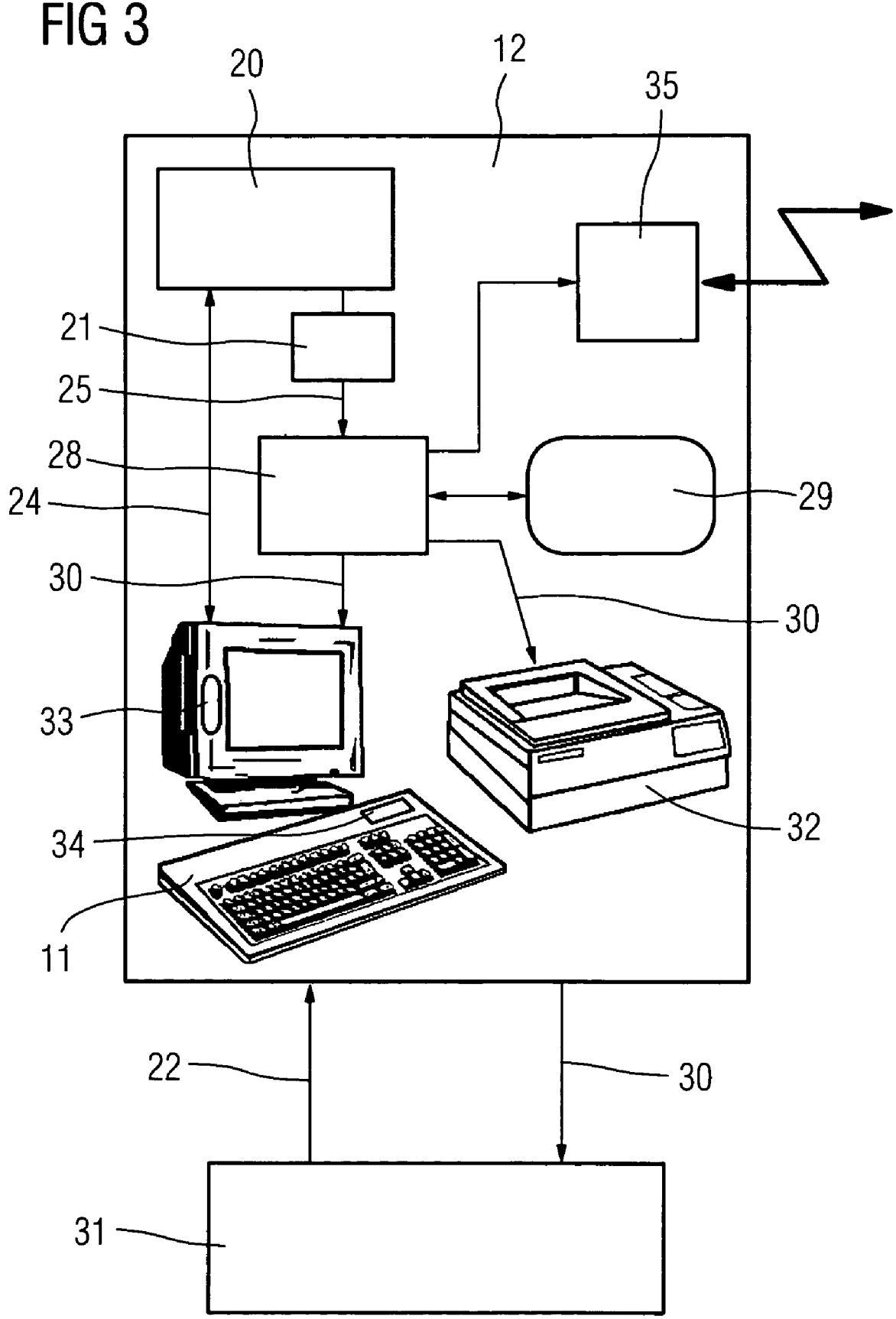

FIG. 3 shows an example workflow in accordance with aspects of the invention (operating concept) in which the device 21 for self analysis of the medical system 12 directs the system-internal status messages 25 to a device 28 for interpretation of system-internal status messages which is connected to the storage means 29, containing technical engineering and application knowledge about the system components. These system-internal status messages 25 are converted into status messages 30 for which no specialist knowledge is required. The medical operating personnel 31 give their instructions 22 on the basis of the status messages 30 reproduced by the operating console 11.

The status messages 30 can be output
visually, e.g. using displays on the monitor of the operating console 11 or projection,
visually e.g. via printout on print media of a printer 32,
acoustically, e.g. by tone modulation (voice) by means of loudspeakers 33 of the operating console 11,
by touch, e.g. via an output device 34 for Braille arranged on the operating console 11,
as a message to the service provider, e.g. via e-mail from the operating console 11 with that error log as an attachment or as voice or text messages via radio networks 35.

In such cases the information contained in the status messages 30 can be as follows:
What is the problem and/or the information?
How seriously is my work affected by it?
What can I do to resolve the problem?
Who can help me to do so?
How can the problem be solved?

The embodiment of the medical device for diagnostics and/or therapy in accordance with the invention resolves the contradiction of information about the system status being present in principle, but of no ad-hoc interpretation of the full scope of such information by the medical user being possible.

The medical user is thus in a position to understand the error messages without the long-winded procedure of acquiring suitable special knowledge. By using the expert knowledge simultaneously provided in a form that they can understand, such users themselves initiate solutions provided for their areas.

In addition they can if required transfer explicit information to the service provider in advance about the error (e.g. by e-mail or SMS). This shortens the time needed to rectify the error, including analysis, procurement of spares and if necessary multiple service calls.

For the provider of the medical service the self-explanatory system analysis means shorter learning phases for staff, breaking down restrictive thresholds since the system communicates with the users at the same language and content level, and that the "experts" are always on hand. Avoiding deviations from the normal status of the system and rectifying them more quickly when they do occur increases the system uptime.

For the providers of services for special systems for medical imaging time and money is saved through to rectification of system deviations. The system also gives the unique competitive advantage of a user-friendly interface.

The current self-analysis functions of a system register deviations from the normal system status and identify these within the system with various cryptic error codes. These error codes are processed in accordance with the invention by a system component (hardware or software) which links the error code to the stored technical engineering and application knowledge. These system components use (everyday) language to output information about the system status and suggestions for remedying deviations on a (system) visual display unit (e.g. operating console, projection, print media, acoustically, sensory).

The invention claimed is:

1. A medical device for diagnostics or therapy, comprising: an analysis device for performing a self-analysis of the medical device and generating a plurality of system-internal status messages based on the self-analysis, wherein informational content of the plurality of system-internal status messages demands having completed a level of training sufficient for a medical personnel user to extract knowledge from the plurality of system-internal status messages, wherein the analysis device is adapted to detect a deviation of an operating status from a standard operating status of the medical device and assign the deviation to a system-internal cryptic error code; a database for storing technical and application knowledge related to the medical device; a processing device for processing the plurality of system-internal status messages with respect to the technical and application knowledge stored in the database, wherein the processing device includes an interpreter to form at least one interpreted status message related to operating the medical system based upon the stored technical and application knowledge, wherein informational content of the at least one interpreted status message is enhanced with technical and application knowledge stored in the database thereby dispensing the medical personnel user with having to complete the training demanded to extract knowledge from the plurality of system-internal status messages; and an operating console for inputting operating instructions and outputting the interpreted status message, wherein operating instructions to the medical personnel user for operating the medical system upon occurrence of at least one system deviation are adjusted by the medical personnel user in response to information contained in the status message formed by the interpreter.

2. The medical device in accordance with claim 1, wherein the interpreted status message includes generally understandable information about the operating status.

3. The medical device in accordance with claim 2, wherein the processing device processes the generally understandable information by merging the cryptic error code with the stored technical and application knowledge.

4. The medical device in accordance with claim 1, wherein the interpreted status message includes a generally understandable suggestion to overcome the deviation.

5. The medical device in accordance with claim 4, wherein the processing device processes the generally understandable suggestion by merging the cryptic error code with the stored technical and application knowledge.

6. The medical device in accordance with claims 1, wherein the interpreted status message is output visually.

7. The medical device in accordance with claim 6, wherein the interpreted status message includes an element chosen from the group consisting of a graphic display, a projection and a printout.

8. The medical device in accordance with claim 1, wherein the interpreted status message is output using sensory means.

9. The medical device in accordance with claim 8, wherein the sensory means include Braille.

10. The medical device in accordance with claim 1, wherein the interpreted status message is output acoustically using a loudspeaker.

11. The medical device in accordance with claim 10, wherein the loudspeaker in arranged on the operating console.

12. The medical device in accordance with claim 1, wherein the interpreted status message is transmitted to a service provider.

13. The medical device in accordance with claim 12, wherein the interpreted status message is transmitted via E-mail.

14. The medical device in accordance with claim 13, wherein the E-mail includes an error log file.

15. The medical device in accordance with claim 14, wherein the error log file is based on the system-internal status message.

16. The medical device in accordance with claim 12, wherein the interpreted status message is transmitted over a radio network.

17. The medical device in accordance with claim 16, wherein the interpreted status message is a voice or a text message.

* * * * *

UNITED STATES PATENT AND TRADEMARK OFFICE
CERTIFICATE OF CORRECTION

PATENT NO.        : 7,698,596 B2
APPLICATION NO.   : 10/981294
DATED             : April 13, 2010
INVENTOR(S)       : Erik Busch It is certified that error appears in the above-identified patent and that said Letters Patent is hereby corrected as shown below:

On the Title Page, Item (73) Assignee's name on issue fee, cancel "Siekens" and substitute --Siemens--.

Signed and Sealed this

Eighth Day of June, 2010

David J. Kappos
*Director of the United States Patent and Trademark Office*